(12) United States Patent
Vetter et al.

(10) Patent No.: US 9,636,028 B2
(45) Date of Patent: May 2, 2017

(54) THREE-DIMENSIONAL NEURAL PROBE MICROELECTRODE ARRAY AND METHOD OF MANUFACTURE

(71) Applicant: NeuroNexus Technologies, Inc., Ann Arbor, MI (US)

(72) Inventors: Rio J. Vetter, Van Buren Township, MI (US); Jamille Farraye Hetke, Brooklyn, MI (US); David S. Pellinen, Ann Arbor, MI (US); Bencharong Suwarato, Ann Arbor, MI (US); Kc Kong, Ann Arbor, MI (US)

(73) Assignee: NEURONEXUS TECHNOLOGIES, INC., Ann Arbor, MI (US)

( * ) Notice: Subject to any disclaimer, the term of this patent is extended or adjusted under 35 U.S.C. 154(b) by 234 days.

(21) Appl. No.: 14/536,867

(22) Filed: Nov. 10, 2014

(65) Prior Publication Data

US 2015/0133761 A1    May 14, 2015

Related U.S. Application Data

(60) Provisional application No. 61/901,783, filed on Nov. 8, 2013.

(51) Int. Cl.
*A61B 5/04* (2006.01)
*A61N 1/05* (2006.01)
(Continued)

(52) U.S. Cl.
CPC ........ *A61B 5/04001* (2013.01); *A61B 5/0478* (2013.01); *A61B 5/6868* (2013.01);
(Continued)

(58) Field of Classification Search
CPC ... A61B 5/0476; A61B 5/0478; A61B 5/6868; A61B 5/6882; A61B 5/04001;
(Continued)

(56) References Cited

U.S. PATENT DOCUMENTS 7,647,097 B2 *  1/2010  Flaherty ............. A61B 5/04001
                                                  600/544
8,121,697 B2 *  2/2012  Greenberg ........... A61N 1/0543
                                                  607/54
(Continued)

FOREIGN PATENT DOCUMENTS

EP          2353636          8/2011

OTHER PUBLICATIONS

McMorland et al. "Baseplate for two-stage cranial monitoring of BMI connectors", J. Neural. Eng.10 (2013), pp. 1-6.*
(Continued)

*Primary Examiner* — Lee S Cohen
(74) *Attorney, Agent, or Firm* — Haynes and Boone, LLP; Taylor Merritt Meacham

(57) ABSTRACT

A three-dimensional neural probe electrode array system is described. Planar probes are microfabricated and electrically connected to flexible micro-machined ribbon cables using a rivet bonding technique. The distal end of each cable is connected to a probe with the proximal end of the cable being customized for connection to a printed circuit board. Final assembly consists of combining multiple such assemblies into a single structure. Each of the two-dimensional neural probe arrays is positioned into a micro-machined platform that provides mechanical support and alignment for each array. Lastly, a micro-machined cap is placed on top of each neural electrode probe and cable assembly to protect them from damage during shipping and subsequent use. The cap provides a relatively planar surface for attachment of a computer controlled inserter for precise insertion into the tissue.

25 Claims, 19 Drawing Sheets

(51) Int. Cl.
*H01R 43/26* (2006.01)
*A61B 5/00* (2006.01)
*A61N 1/04* (2006.01)
*A61B 5/0478* (2006.01)

(52) U.S. Cl.
CPC ......... *A61N 1/0456* (2013.01); *A61N 1/0472* (2013.01); *A61N 1/0529* (2013.01); *A61N 1/0539* (2013.01); *H01R 43/26* (2013.01); *A61B 5/6882* (2013.01); *Y10T 29/49169* (2015.01)

(58) Field of Classification Search
CPC .. A61N 1/0529; A61N 1/0531; A61N 1/0534; A61N 1/0539
USPC .................. 600/377, 378, 544; 607/116, 139
See application file for complete search history.

(56) References Cited

U.S. PATENT DOCUMENTS

| | | | |
|---|---|---|---|
| 8,255,061 B2* | 8/2012 | Perlin | A61B 5/04001 600/377 |
| 8,560,041 B2* | 10/2013 | Flaherty | A61B 5/0031 600/372 |
| 8,824,156 B2* | 9/2014 | Tai | A61B 5/0031 361/752 |
| 2004/0082875 A1 | 4/2004 | Donoghue et al. | |
| 2005/0033378 A1 | 2/2005 | Sheffield et al. | |
| 2005/0283203 A1 | 12/2005 | Flaherty et al. | |
| 2007/0007240 A1 | 1/2007 | Wise et al. | |
| 2010/0125312 A1 | 5/2010 | Stevenson et al. | |
| 2011/0125001 A1 | 5/2011 | Fang et al. | |
| 2012/0277834 A1* | 11/2012 | Mercanzini | A61B 5/04001 607/62 |
| 2013/0157498 A1 | 6/2013 | Scholvin et al. | |
| 2013/0172774 A1* | 7/2013 | Crowder | A61B 5/04 600/544 |

OTHER PUBLICATIONS

Musallam et al, "A floating metal microelectrode array for chronic implantaion", Journal of Neuroscience Method 160 (2007) pp. 122-127.*
EPSEARCH, "14192442", Mar. 10, 2012, Mar. 10, 2015.
"EP Extended European Search", Application No. 14192442.3, Jul. 6, 2015.
Bai, et al., "A High-Yield Microassembly Structure for Three-Dimensional Microelectrode Arrays", IEEE Transactions on Biomedical Engineering, vol. 47, No. 3, Mar. 2000.
Hetke, et al., "3-D Silcon Probe Array with Hybrid Polymer Interconnect for Chronic Cortical Recording", Department of Electrical Enginerring and Computer Science, Department of Biomedical Engineering, University of Michigan, Ann Arbor, MI, USA; Department of Neurosurgery, University of Wisconsin, Madison, WI, USA, 1-4.
Hoogerwerf, et al., "A Three-Dimensional Microelectrode Array for Chronic Neural Recording", IEEE Transactions on Biomedical Engineering, vol. 41, No. 12, Dec. 1994.
Ruther, et al., "The Neuroprobes Project—Multifunctional Probe Arrays for Neural Recording and Stimulation", Proc. of the 13th Annual Conf. of the IFESS, Sep. 21-25, 2008, Freiburg, Germany; Biomed. Tech., vol. 53 (2008) Suppl. 1, (c) 2008 by Walter de Gruyter, Berlin, New York, 238-240, 2008, 238-240.
Yao, et al., "A Microassembled Low-Profile Three-Dimensional Microelectrode Array for Neural Prosthesis Applications", Journal of Microelectromechanical Systems, Vo. 16, No. 4, Aug. 2007, 977-988.

* cited by examiner

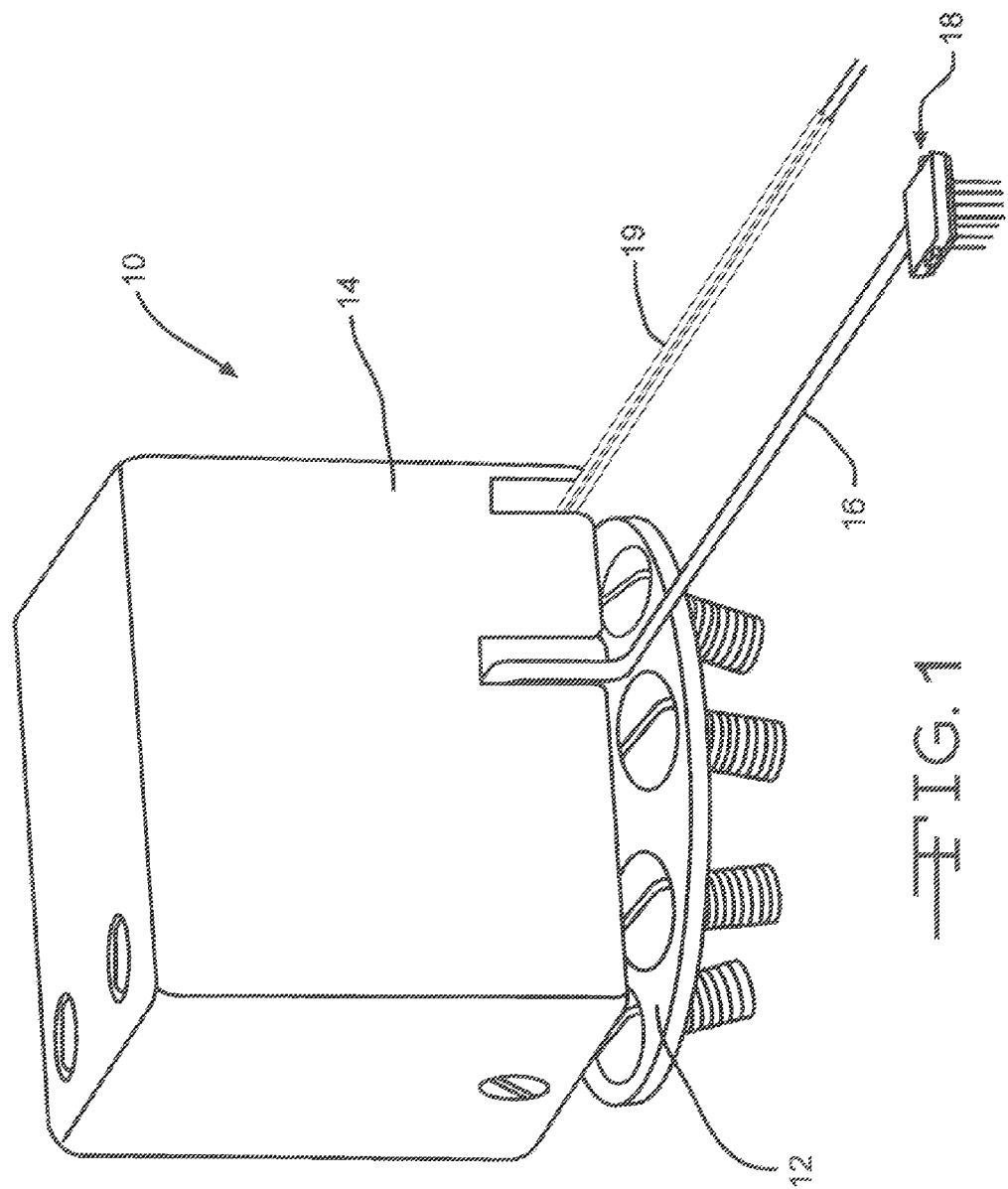

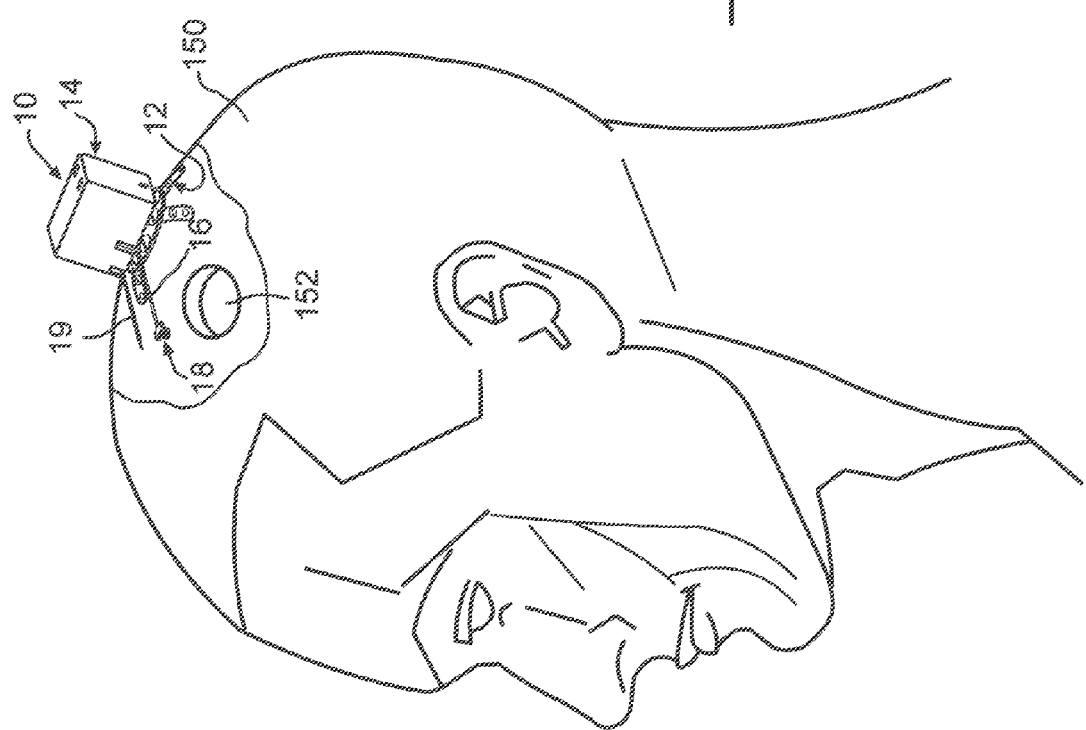

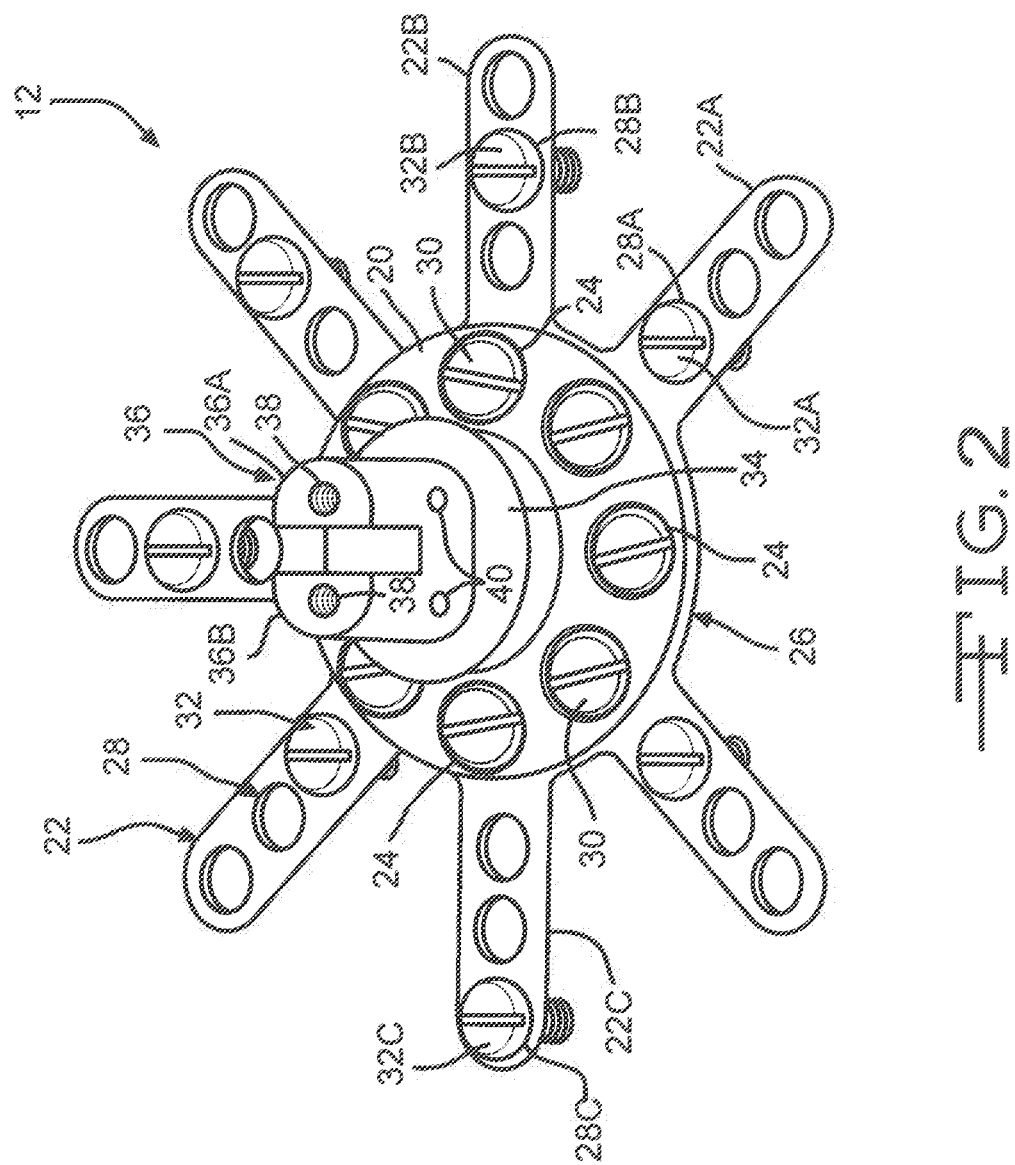

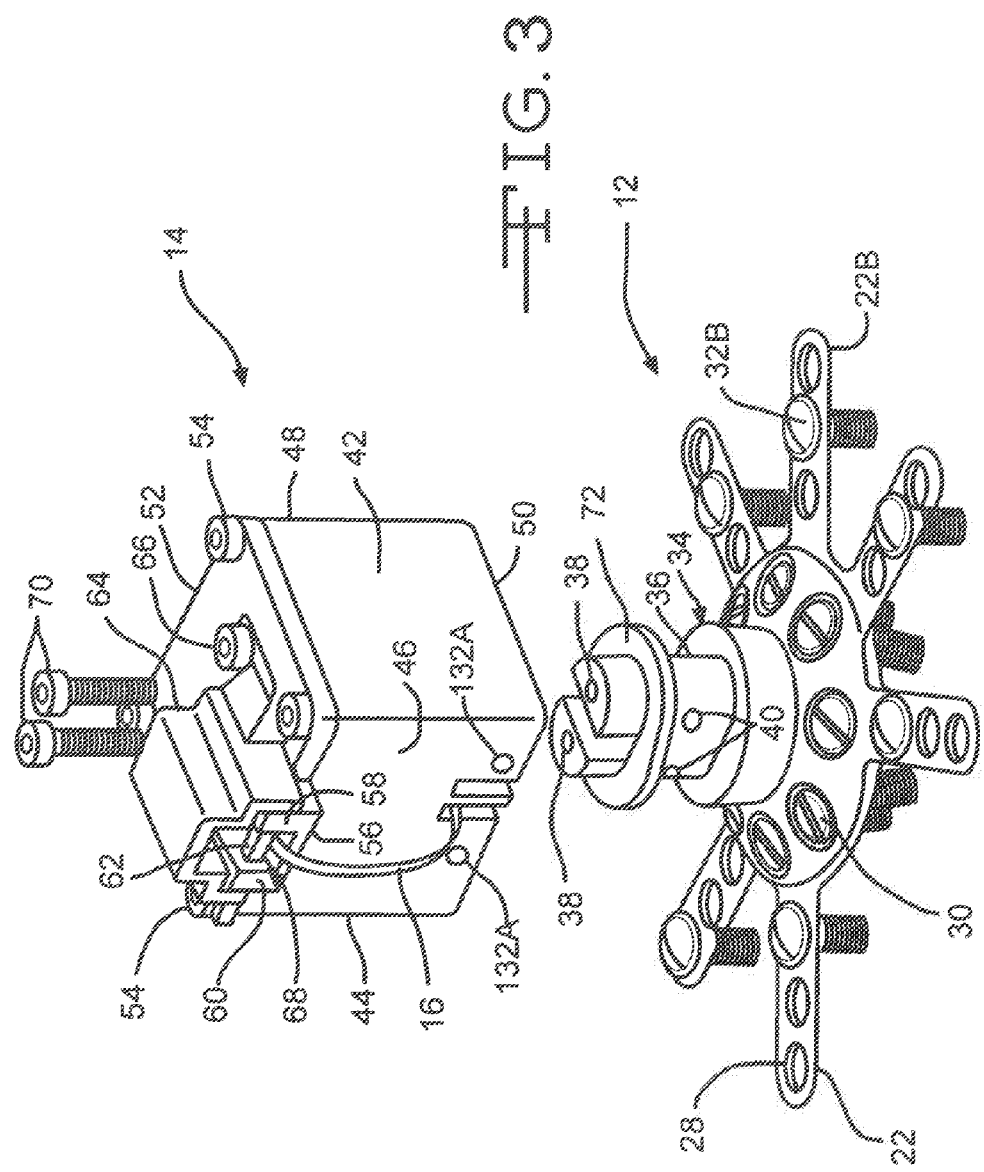

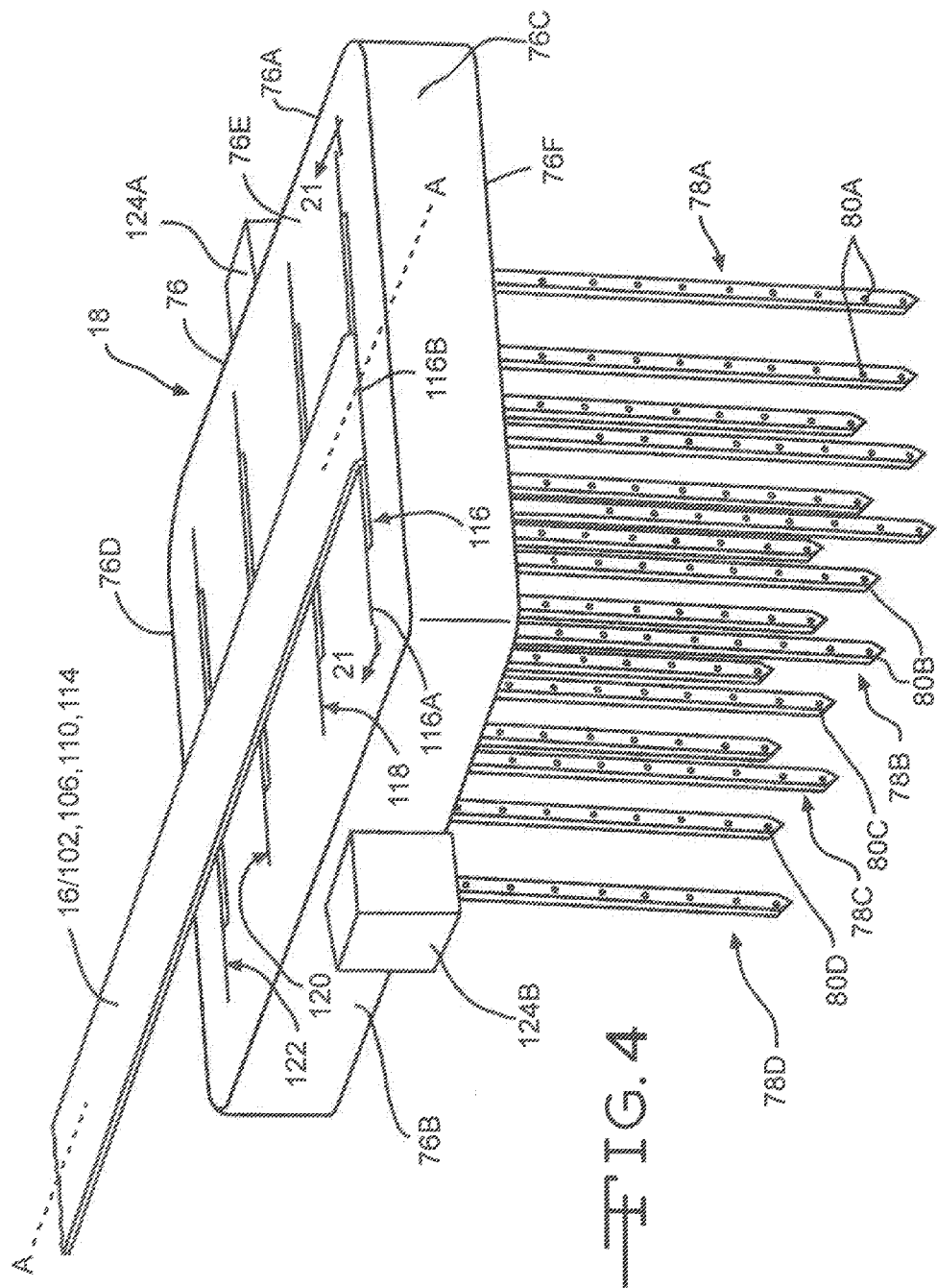

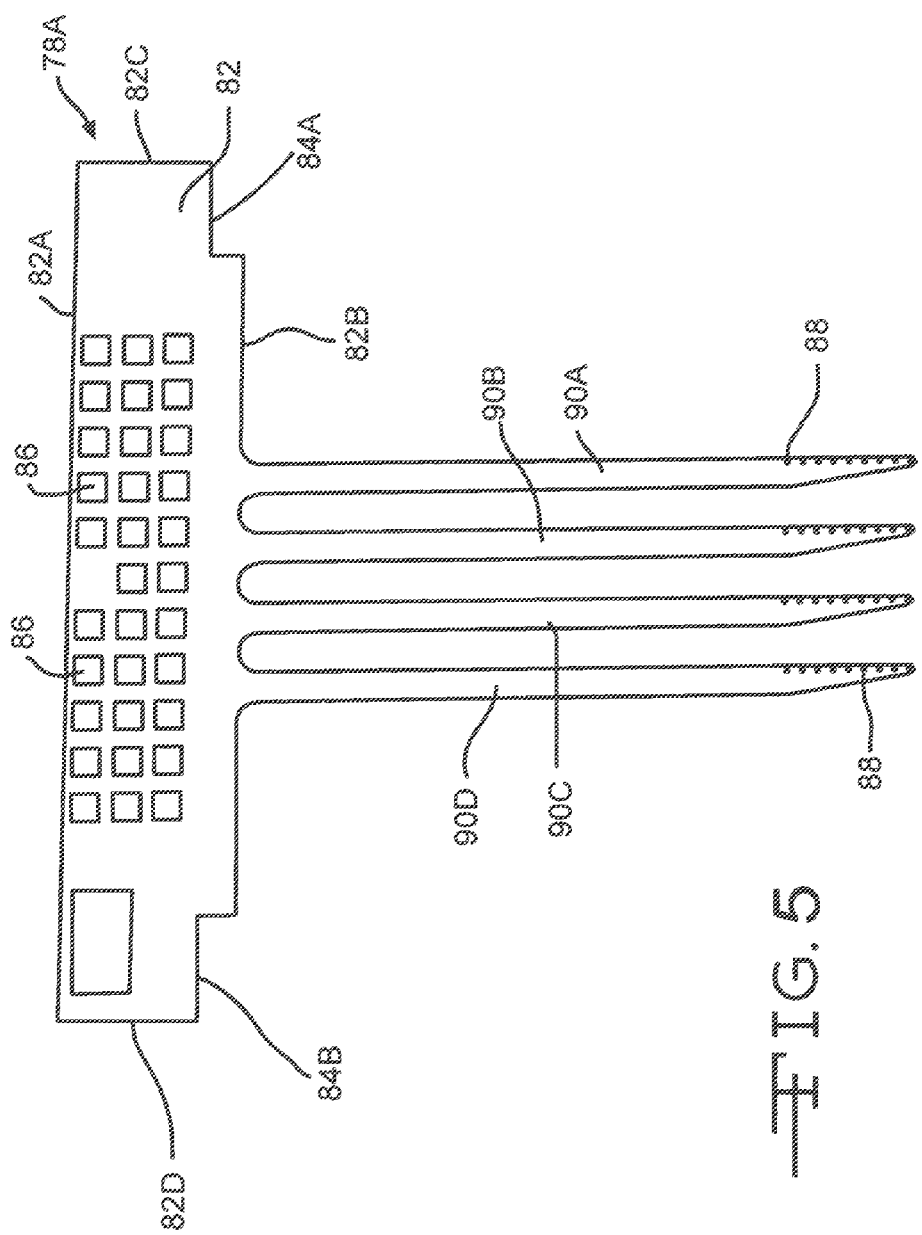

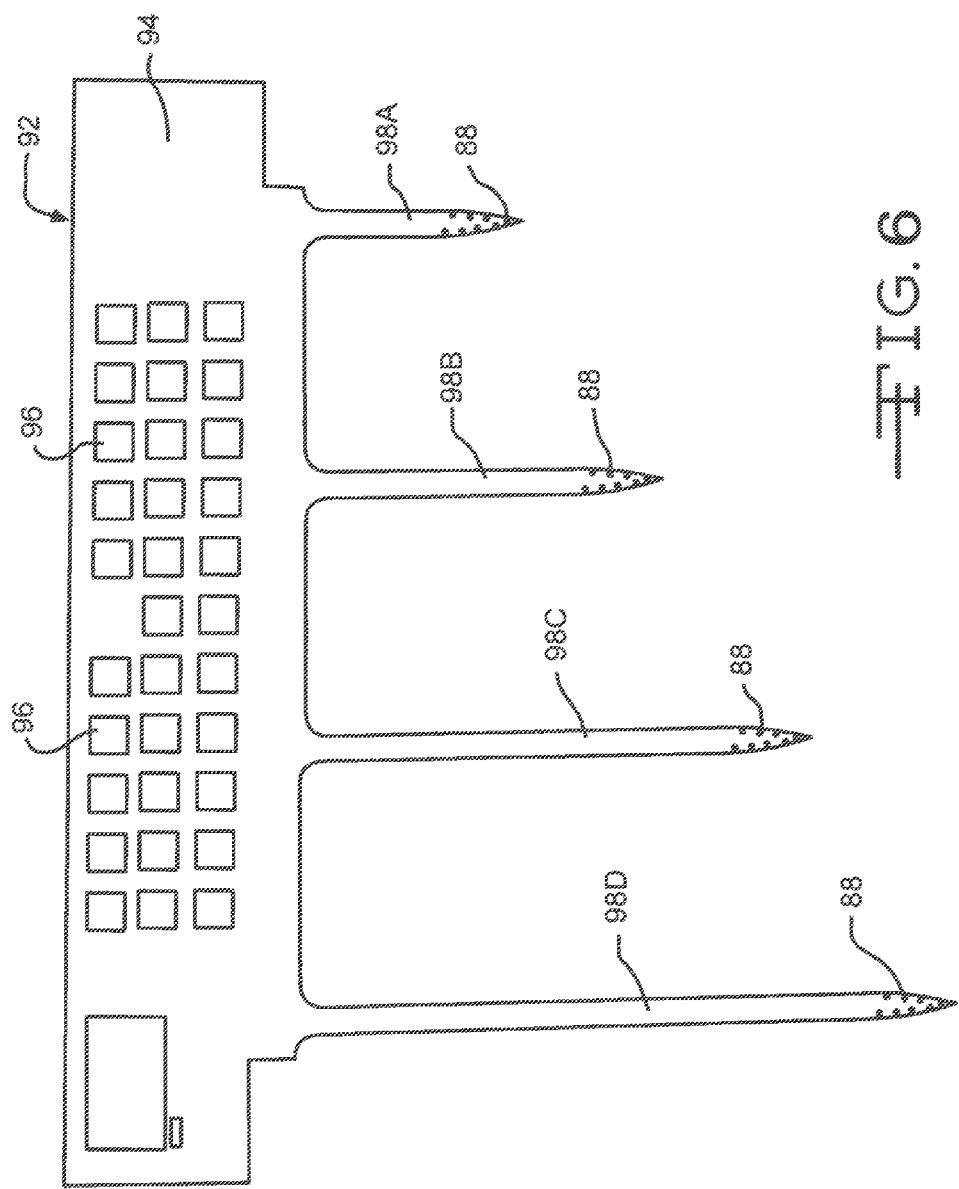

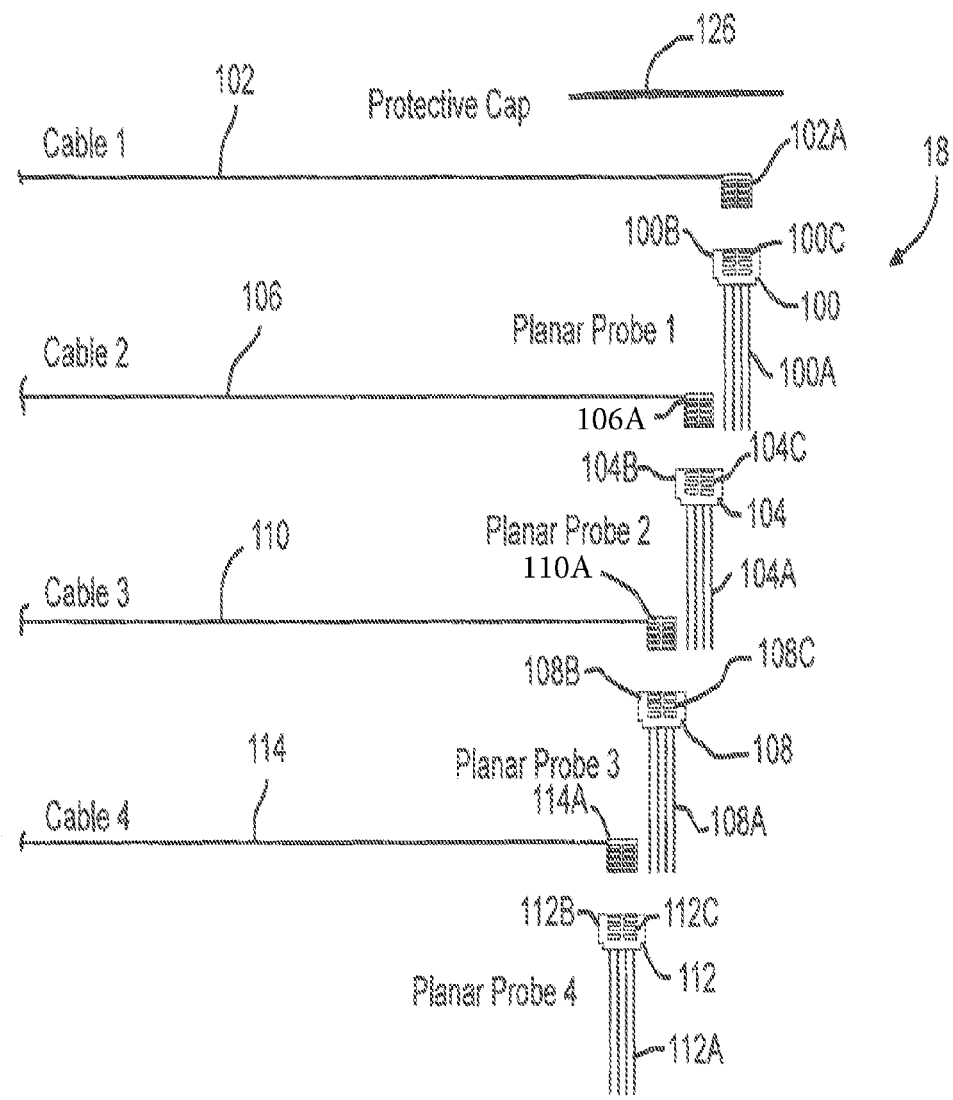
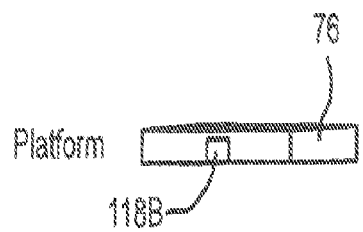
FIG. 7

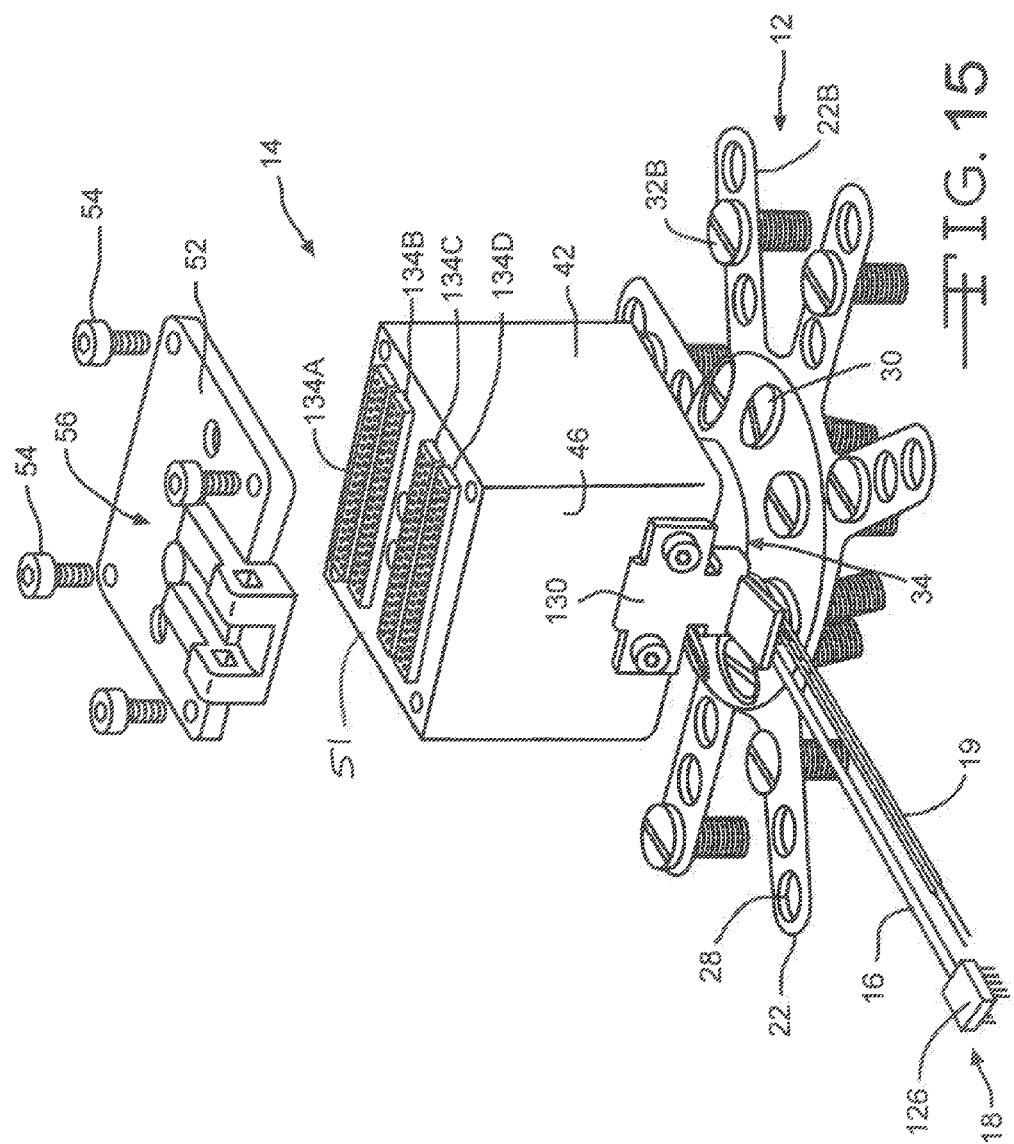

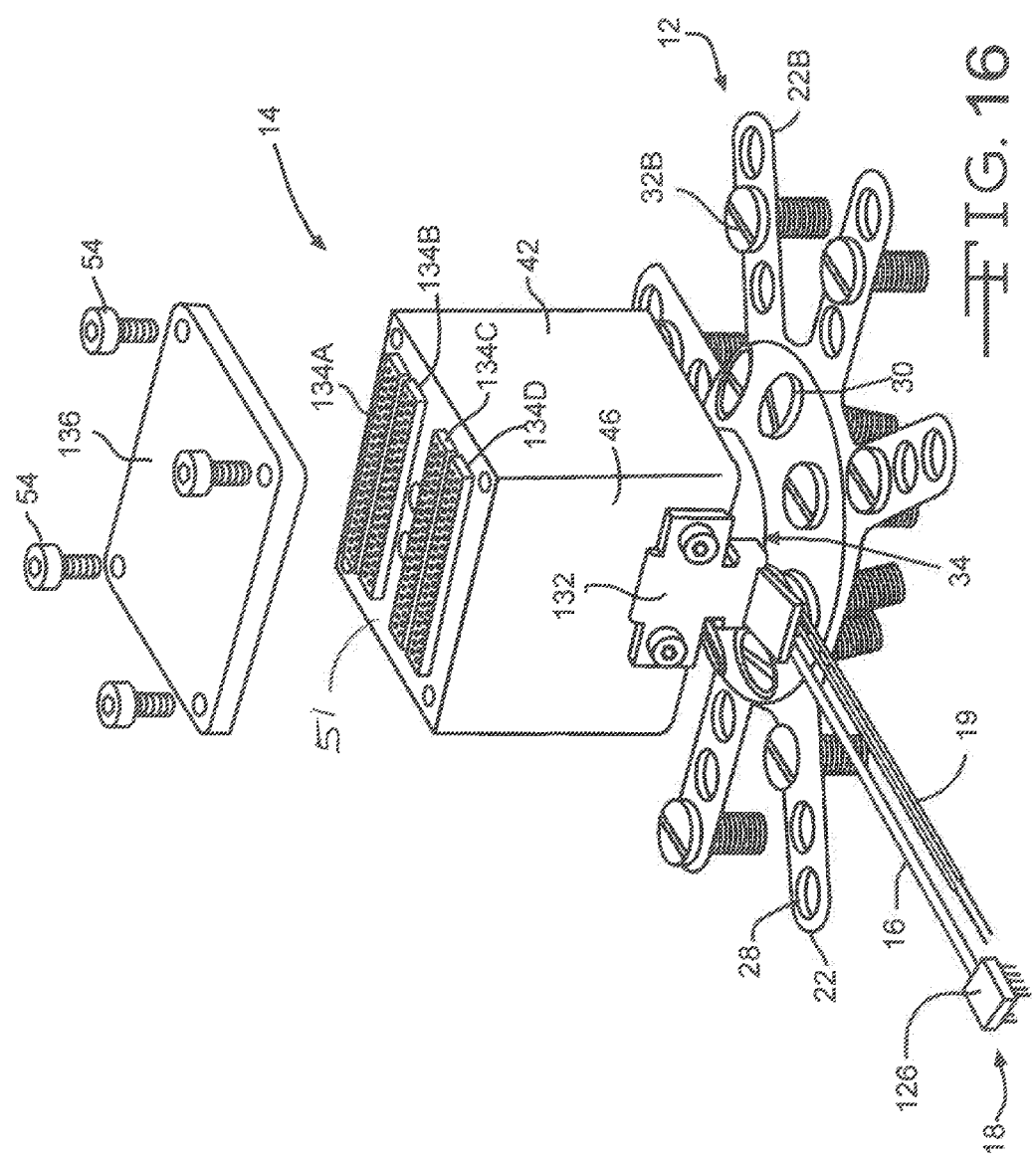

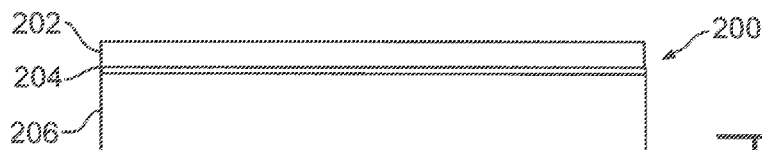
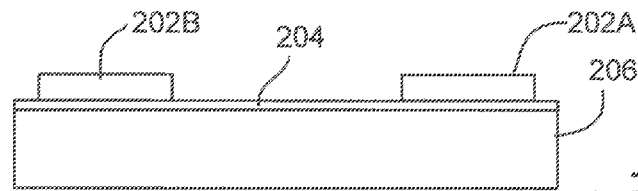
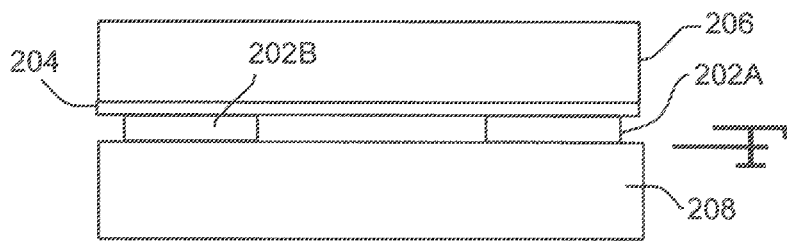
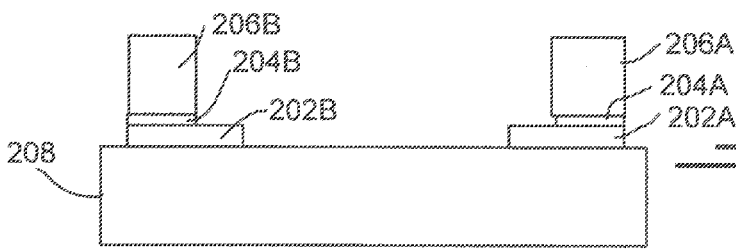
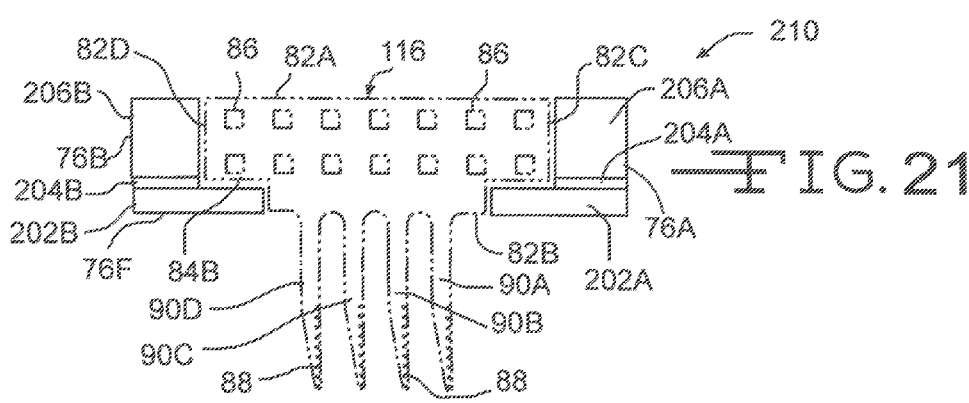

THREE-DIMENSIONAL NEURAL PROBE MICROELECTRODE ARRAY AND METHOD OF MANUFACTURE

CROSS-REFERENCE TO RELATED APPLICATIONS

This application claims priority from U.S. Provisional Application Ser. No. 61/901,783, filed on Nov. 8, 2013.

BACKGROUND OF THE INVENTION

1. Field of the Invention

The invention relates to the field of devices and methods used for neural interventions.

2. Prior Art

The conventional method used to interface the nervous system includes a multi-contact electrode array. Electrode arrays are designed to transmit signals into the tissue ("stimulation") or extract signals from the tissue ("sense"). These electrode arrays are commonly used in neuroscience and neurophysiological research as well as in clinical therapeutic applications. Often, a precise volume of tissue in the peripheral nervous system or in the central nervous system is the target for placement of the electrode array. Additionally, it is desirable to interface with the targeted volume in three-dimensions. Commercially available electrode arrays are limited in their ability to position electrode contacts in a three-dimensional arrangement. Two examples are the planar silicon array, often referred to as the "Michigan Probe" and an alternative silicon-based technology referred to as the "Utah Array". The Michigan Probe is limited to positioning electrode contacts in a two-dimensional arrangement, all within a single plane. The Utah Array is also limited to positioning electrode contacts in a two-dimensional plane. Moreover, electrode contacts in a Utah Array are limited to placement on the tip of each electrode shank.

The present invention presents a method for creating a true three-dimensional arrangement of electrode contacts using two or more two-dimensional planar silicon microelectrode arrays. The planar electrode arrays are aligned in rows to provide a three-dimensional tissue interface. There is prior art where researchers have constructed three-dimensional microelectrode arrays using various methods, but the present invention is a novel approach using a multitude of planar neural electrode probes combined to make a customizable and scalable three-dimensional array.

SUMMARY OF THE INVENTION

The present invention provides a structure for stimulation and sensing of neurophysiological signals from an array of microelectrode contacts positioned in a three-dimensional arrangement. This provides a "richer" communication pathway to and from the neural circuit of interest.

The primary advantage is that the present invention describes a method of creating a three-dimensional electrode tissue interface using multiple neural probe electrode arrays consisting of two or more planar probes arranged in side-by-side electrically connected to flexible ribbon cables. The multiple neural probe electrode arrays are supported by a pedestal to thereby provide a plurality of neural electrode probes in an "x" and "y" configuration, for example a 4×4 array of neural electrode probes. Additionally, each probe has a number of stimulation or sensing electrodes along its "z" length. This effectively provides a three-dimensional stimulation or sensing array. Any one of a number of neural electrode arrays can be designed for a desired application. In that respect, the present invention leverages a long standing history of a proven technology (i.e., planar neural electrode probes, but arranged into an x, y and z configuration) and is a method that is scalable and customizable with regards to the geometry, size and number of electrode contacts.

A three dimensional electrode array configuration is important for many reasons. One example is when considering interfacing with the cortex where neurons are structured in an inhomogeneous manner that differs anatomically and physiologically across ventral/dorsal and medial/lateral directions. Neurons in the cortex are generally oriented vertically. Being able to arrange electrode contacts across depths provides more tolerance in positioning to help ensure that a richest signal can be obtained. This also allows positioning of electrode contacts at multiple points along a single neuron, for example spanning the distance from a particular neuron's cell body to its respective dendritic tree. Neurons in the cortex are organized in columns where cells within a specific column perform similar functions and these functions may differ between columns. Therefore, a three-dimensional arrangement (x, y and z) of contacts has the ability to span multiple neuronal columns.

These and other objects will become apparent to one of ordinary skill in the art by reference to the following description and the appended drawings.

BRIEF DESCRIPTION OF THE DRAWINGS

FIG. 1 is a perspective view of a neural probe electrode array system 10 according to the present invention.

FIG. 1A is a perspective view of the neural probe electrode array system 10 shown in FIG. 1 mounted to a skull 150 adjacent to a craniotomy opening 202.

FIG. 2 is a perspective view of a skull mounting plate 12 of the neural probe system 10.

FIG. 3 is a perspective view showing an electronics housing 14 separated from the skull mounting plate 12 of the neural probe system 10.

FIG. 4 is a perspective view of an exemplary embodiment of a neural probe electrode assembly 18 according to the present invention.

FIGS. 5 and 6 are front elevational views of exemplary neural probe electrode arrays 78A and 92, respectively.

FIG. 7 is an exploded view of a 4×4 neural probe electrode assembly 18 according to the present invention.

FIGS. 15 and 16 are perspective views of the neural probe system 10 shown in FIG. 14, but with the shipping cover 52 being removed and replaced by permanent cover 136.

FIGS. 17 to 21 illustrate of an exemplary process for manufacturing the platform 76 for the neural probe assembly 18.

DETAILED DESCRIPTION OF THE PREFERRED EMBODIMENTS

Figure 8:
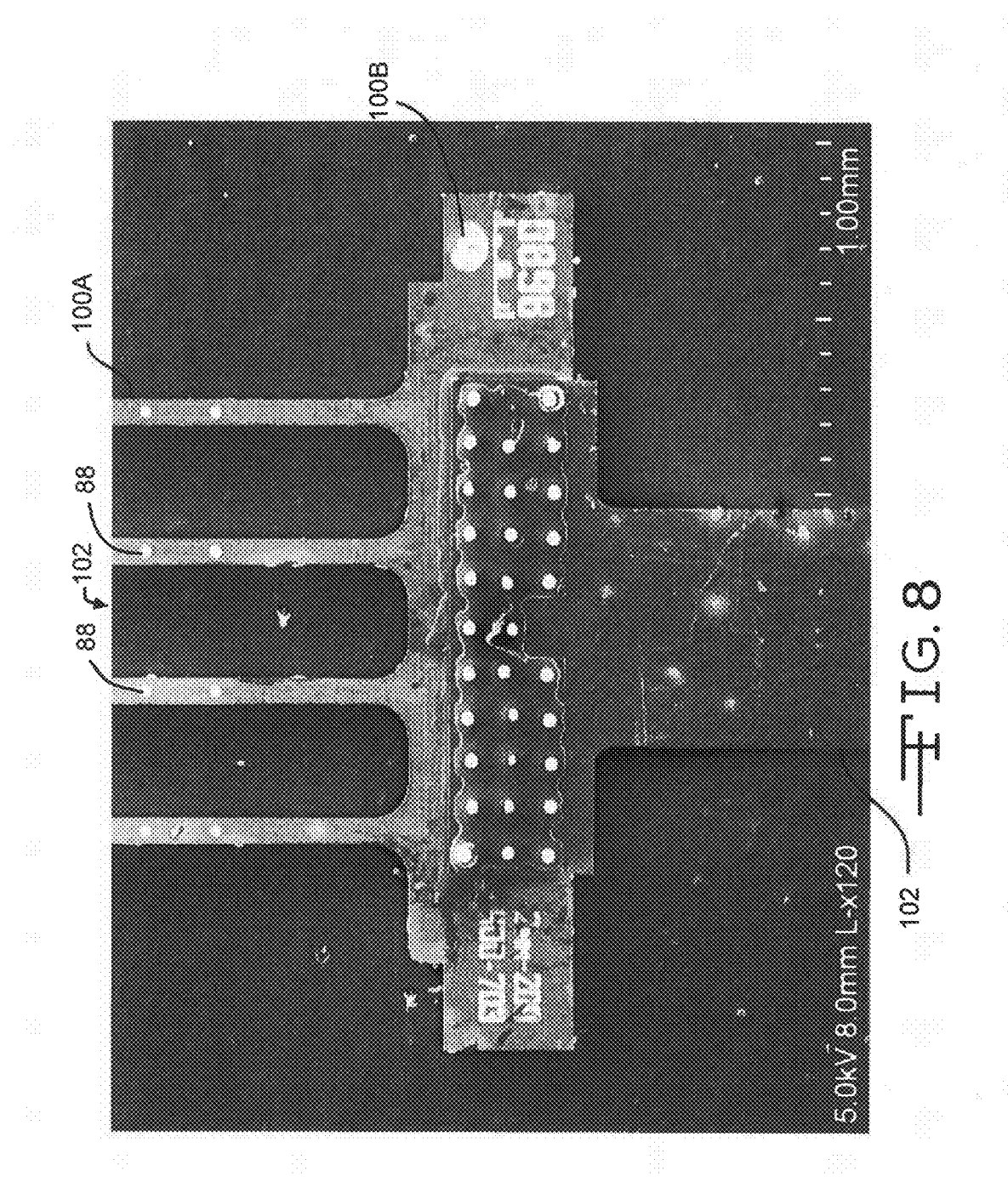
FIGS. 8 and 9 are photographs showing rivets connecting the bond pads of a neural electrode probe 100 to a ribbon cable 102.

Turning now to the drawings, FIG. 1 is a perspective view of a neural probe electrode array system 10 according to the present invention. The neural probe system 10 comprises a skull mounting plate 12 supporting an electronics housing 14. A flexible ribbon cable 16 connects from electronics (see connectors 134A to 134D in FIGS. 15 and 16) in the housing 14 to a neural probe electrode assembly 18. A neural probe electrode assembly 18 according to the present invention includes at least one, and preferably a plurality of neural probe electrode arrays as exemplified in FIGS. 5 and 6. The housing 14 further includes wires 19 for grounding the subject. These wires not only ground the animal, but may be used as a reference when performing differential recording, or as a return path for current when stimulating.

FIG. 2 illustrates the skull mounting plate 12 comprising a curved mount body 20 supporting a plurality of extending legs 22. The curved body 20 is a dome-shaped member having a plurality of first, unthreaded openings 24 adjacent to a perimeter 26 thereof. Preferably the first openings 24 are at regularly spaced intervals. Legs 22 extend from the perimeter 26 and provide a number of second, unthreaded openings 28. While not necessary, the second openings 28 are illustrated as being spaced at regular intervals along the length of each leg 22. Seven legs 22 are shown, but that is not necessary. There can be more or less than that number of legs.

FIG. 2 further illustrates that first screws 30 are received in the first unthreaded openings 24 in the dome-shaped body 20 and second screw 32 are received in the second unthreaded openings 28 in the legs 22. Moreover, the second screws 32 can be positioned in any one of the three second openings 32 of each leg 22. Leg 22A shows screw 32A positioned in a first leg opening 28A adjacent to the mount body 20, leg 22B shows screw 32B positioned in a second opening 28B and leg 22C shows screw 32C positioned in a third, most distal opening 28C. If desired, the legs 22 can be cut to shorten their lengths and thereby eliminate some or all of the leg openings 28 as desired for a particular surgical procedure. FIG. 1 shows an exemplary embodiment where the skull mounting plate is devoid of any legs 22. The legs 22 can also be bent to match the curvature of a skull.

It is noted that the length of first screws 30 is desirably somewhat longer than that of the second screws 32. The first screws 30 are of a sufficient length to provide first threads screwed into the skull or cranium bone to accommodate for the offset distance of the mount body 20 from a skull as a result of its dome shape. That is in comparison to the legs 22, which are relatively closely spaced to the skull. In any event, screws 30, 32 have threads that are configured for threading into the skull 150 (FIG. 1A). In one embodiment according to the present invention, the first screws 30 are 2.4 mm wide×6 mm long and the second screws 32 are 2 mm wide×4 mm long. The screws 30, 32 are preferably titanium.

The skull mounting plate 12 has a cylindrical-shaped pedestal 34 extending upwardly from the dome-shaped mount body 20. A U-shaped yoke 36 is supported on an upper face of the pedestal 34. A threaded opening 38 is provided into the depth of each arm 36A, 36B of the yoke. There is also a threaded opening 40 extending into the depth of each arm 36A, 36B adjacent to the pedestal 34. Preferably, the threaded openings 38 and 40 do not intersect each other.

FIG. 3 illustrates the electronics housing 14 just prior to being mounted to the skull mounting plate 12. In one embodiment according to the present invention, the electronics housing 14 is a rectangular-shaped member of a biocompatible metal, such as titanium. As those of skill in the art will readily understand, the shape of electronics housing 14 illustrated in the drawings is exemplary and should not limit the scope of the present invention. Other shapes for the electronics housing 14 may be desired for a particular surgical procedure or application.

In the illustrated embodiment, the electronics housing 14 comprises right and left sidewalls 42 and 44 meeting front and back sidewall 46 and 48, all extending to a bottom wall 50 and a top wall 51 (FIGS. 15 and 16). A shipping cover plate 52 is temporarily secured to the upper edges of the right, left, front and back sidewalls using screws 54 threaded into receptacles therein.

Figure 11:
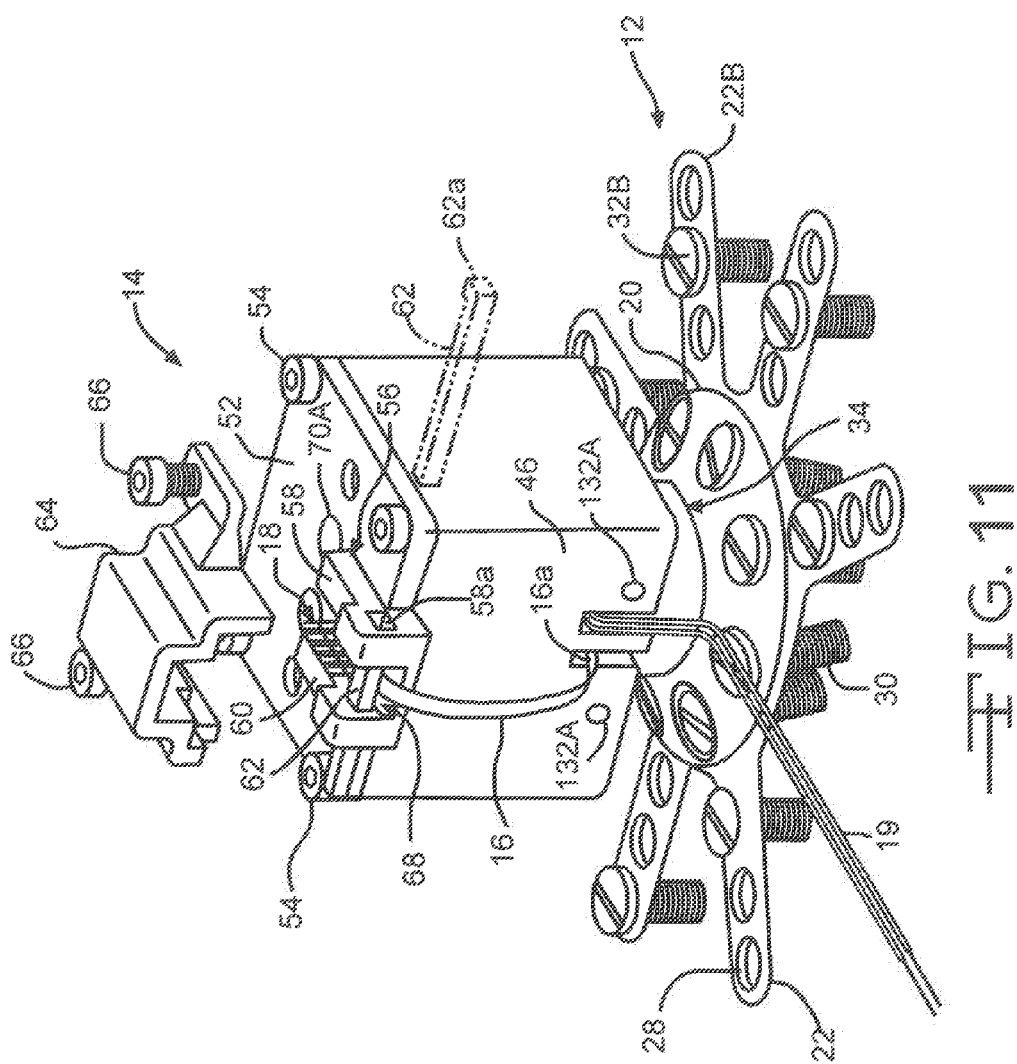
FIG. 11 is a perspective view of neural probe electrode array system 10 shown in FIG. 1 just prior to removal of the electrode assembly 18 from its cradle 56 on the electronics housing 14.

The shipping cover plate 52 supports a cradle 56 for the neural probe assembly 18. The cradle 56 comprises spaced apart webs 58 and 60 that are aligned perpendicular to the front sidewall 46. Enlarged portions of the webs 58, 60 extending out past the front sidewall 46 support a guard bar 62 received in openings in the webs 58, 60. The guard bar 62 has an L-shaped end 62A that nests in a recess 58A of web 58 (FIG. 11). The L-shaped end 62A acts as a stop so that the guard bar 62 cannot be moved completely through the web openings.

A shaped secondary cover 64 is supported on the cradle 56 by screws 66 threaded into the shipping cover plate 52. With the secondary cover 64 mounted to the shipping cover plate 52 over cradle 56, there is a forwardly facing opening 68 underneath guard bar 62. The significance of opening 68 will be described in detail hereinafter.

FIG. 3 further illustrates the electronics housing 14 just prior to it being mounted on the cylindrical pedestal 34 of the skull mounting plate 12. The bottom wall 50 of the electronics housing 14 has an opening (not shown) configured to receive the yoke 36. With the electronics housing 14 supported on the skull mounting plate 12, screws 70 are received through oversized openings 70A (FIGS. 11 to 14) in the cover plate 52 and threaded into openings 38 in the yoke arms 36A, 36B adjacent to the cylindrical pedestal 34. That way, the cover plate 52 can be removed from the housing 14 without having to disconnect the electronics housing from the skull mounting plate 12.

Those skilled in the art will readily understand that the electronics housing 14 can be secured to the skull mounting plate 12 by means other than screws 70 threaded into the yoke 36. For example, the yoke could be replaced with a threaded post and the housing could have a matching opening in its bottom wall for threadingly connecting the housing 14 to the mounting plate 12. A ball and detent connection can also be used.

A silicone gasket 72 is disposed between the electronics housing and the skull mounting plate. That is for the purpose of providing a fluid barrier as well as cushioned connection between the housing 14 and pedestal 34. The gasket 72 also serves as a barrier when skin is cinched up against the pedestal 34, but underneath the electronics housing 14 during a surgical procedure.

FIG. 4 is an enlarged view of the ribbon cable 16 connected to a neural probe electrode assembly 18. The ribbon cable is designed to be flexible so that the neural probe electrode assembly is virtually untethered from the electronics housing. This allows the neural probe electrode assembly to "float" with the brain during brain pulsation or brain shift. The ribbon cable may be a thin-film based cable like those made from polyimde, parylene, or silicone with embedded conductors (e.g., gold, platinum, etc.).

The neural probe electrode assembly 18 comprises a probe platform 76 supporting a plurality of neural probe electrode arrays. Four neural probe electrode arrays 78A, 78B, 78C and 78D are shown with each array having four neural probes 80A, 80B, 80C and 80D.

FIG. 5 shows that the exemplary thin-film neural probe electrode array 78A comprises a proximal bond pad plate 82 (e.g., titanium/gold stack) connected to buried conductive traces that run along each shank 90A, 90B, 90C and 90D (e.g., titanium/gold/platinum stack) to connect to the electrode contacts 88 (e.g., titanium/gold/platinum stack).

The bond pad plate has an upper edge 82A spaced from a lower edge 82B, both the upper and lower edges meeting spaced apart right and left edges 82C and 82D. A step 84A resides where the right edge 82C meets the lower edge 82B. An opposed step 84B resides where the left edge 82D meets the lower edge 82B. Plate 82 supports a plurality of bond pads 86 that are electrically connected to a respective one of the plurality of electrodes 88 supported on a shank by buried conductive traces. The exemplary neural probe electrode array 78A has four equally spaced apart shanks 90A, 90B, 90C and 90D extending distally from the plate 82. The shanks are of equal lengths.

While not shown in the drawing, each thin-film neural probe electrode array according to the present invention is comprised of multiple metal traces and electrode sites. As many as 100 conductive traces and electrode sites can be realized on an array that is as narrow as 30 microns and as thin as 6 microns. In order to be strong enough to be inserted into tissue, these neural probe electrode arrays must be either integrated during fabrication on a carrier that provides strength, or attached to a strengthening carrier post-fabrication. If the strengthening carrier is stiff, the electrode array can be inserted into tissue along a desired axial direction of a guiding element. Moreover, the electrode array shanks have pointed tips, which help reduce the tissue resistance to insertion.

FIG. 6 illustrates another embodiment of a neural probe electrode array 92 comprising a bond plate 94 supporting bond pads 96. Four equally spaced apart electrode shanks 98A, 98B, 98C and 98D depend from the bond plate. In this exemplary array, the shanks are of unequal lengths. Those skilled in the art will readily understand that a neural probe array according to the present invention can have more or less than four electrode shanks. If there are two or more shanks, but not one, they can be of the same or different lengths. If there are three or more electrode shanks, but not two or one, they can be equally or unequally spaced apart from each other. Moreover, any one shank can support more or less electrodes 88 than another shank.

FIG. 7 is an exploded view illustrating a 4×4 neural probe electrode assembly 18 (four neural probes having four electrode shanks each). The first neural probe array 100 has four electrode shanks 100A extending from bond plate 100B. Bond plate 100B supports bonds pads 100C which are physically and electrically connected to cable bond pads 102A at a distal end of a first flexible ribbon cable 102. The second neural probe array 104 has four electrode shanks 104A extending from bond plate 104B. Bond pads 104C supported on plate 104B are physically and electrically connected to cable bond pads 106A at a distal end of a second flexible ribbon cable 106. The third neural probe array 108 has four electrode shanks 108A extending from bond plate 108B. Bond pads 108C supported on plate 108B are physically and electrically connected to cable bond pads 110A at a distal end of a third flexible ribbon cable 110. Finally, the fourth neural probe array 112 has four electrode shanks 112A extending from bond plate 112B. Bond pads 112C supported on plate 112B are physically and electrically connected to cable bond pads 114A at a distal end of a fourth flexible ribbon cable 114.

Referring back to FIG. 4, the probe platform 76 of the neural probe electrode assembly 18 comprises right and left sidewalls 76A and 76B extending to distal and proximal sidewalls 76C and 76D. The sidewalls 76A, 76B, 76C and 76D extend to an upper face wall 76E and a lower face wall 76F. There are four slots 116, 118, 120 and 122 extending through the thickness of the platform from the upper face wall 76E to the lower face wall 76F thereof. The slots are aligned parallel to each other and to the distal and proximal sidewalls 76C, 76D. The four slots extend to, but do not meet the right and left sidewalls 76A, 76B. While four slots are shown, that is by way of example. Moreover, the slots need not be parallel to each other. Instead, they can be aligned at an angle other than 180° with respect to each other.

Slot 116 is exemplary of the other slots. It comprises a proximal slot portion 116A of a width extending toward the right and left sidewalls 76A, 76B that is longer than the width of a distal slot portion 116B. However the proximal slot portion 116 is of a lesser depth measured along axis A-A intersecting the distal and proximal sidewalls 76C, 76D than the depth of distal slot portion 116B.

Figure 9:
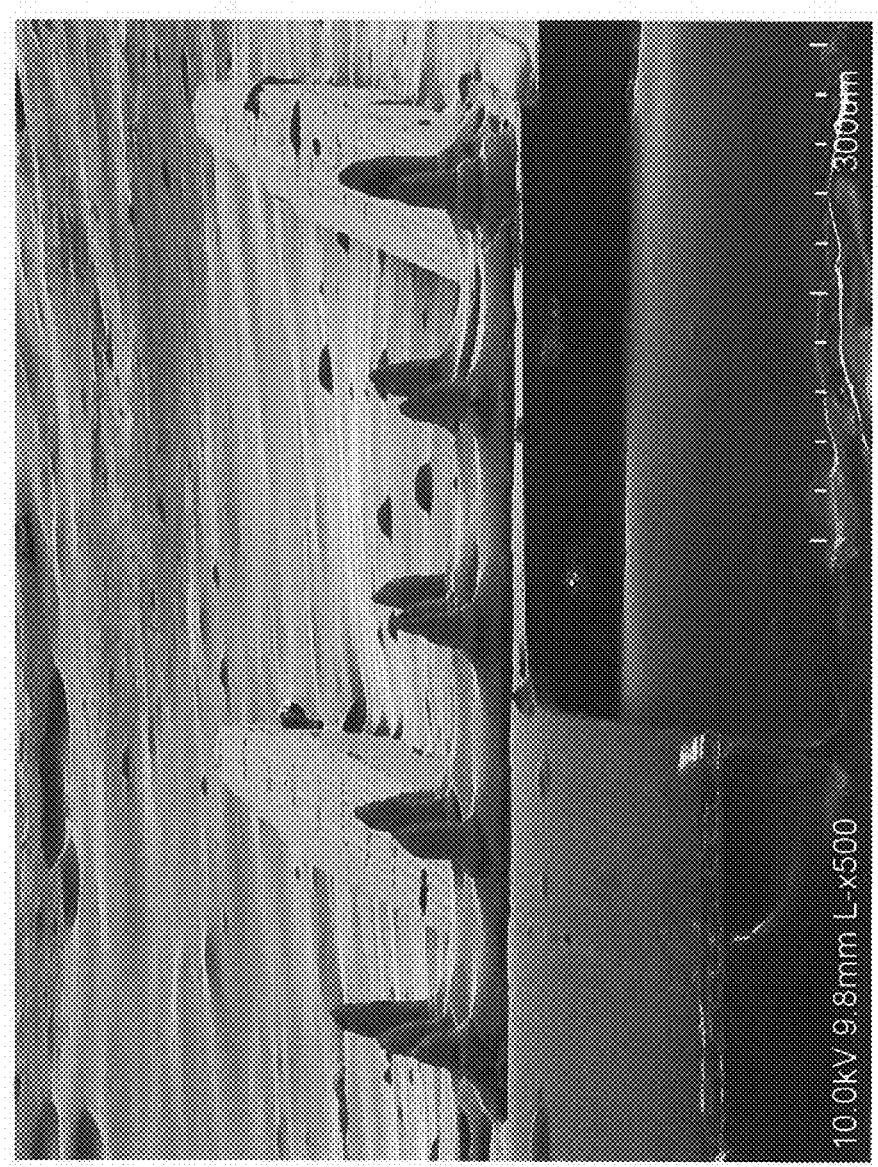

With reference to the exemplary schematic shown in FIG. 7, FIGS. 8 and 9 are photographs showing rivets connecting the bond pads 100C on bond plate 100B of neural electrode probe array 100 to the cable bond pads 102A at the distal end of ribbon cable 102. The increased width of the distal slot portion 116B accommodates these rivet connections when the neural probe array 100 is seated into slot 116. Moreover, the distal slot portion 116 extends completely through the thickness of the platform, but the proximal slot portion 116A does not. The steps 84A, 84B of bond plate 82 (FIG. 8) register where the proximal and distal slot portions 116A, 116B meet inside the platform 76. In this position, the neural probe array 100 is aligned perpendicular to axis A-A. With the first to fourth neural probes 78A, 78B, 78C and 78D received in the respective first, second, third and fourth slots 116, 118, 120 and 122 in platform 76, the respective neural probe flexible ribbon cables 102, 106, 110 and 112 lay over the upper platform face wall 76E.

Figure 10:
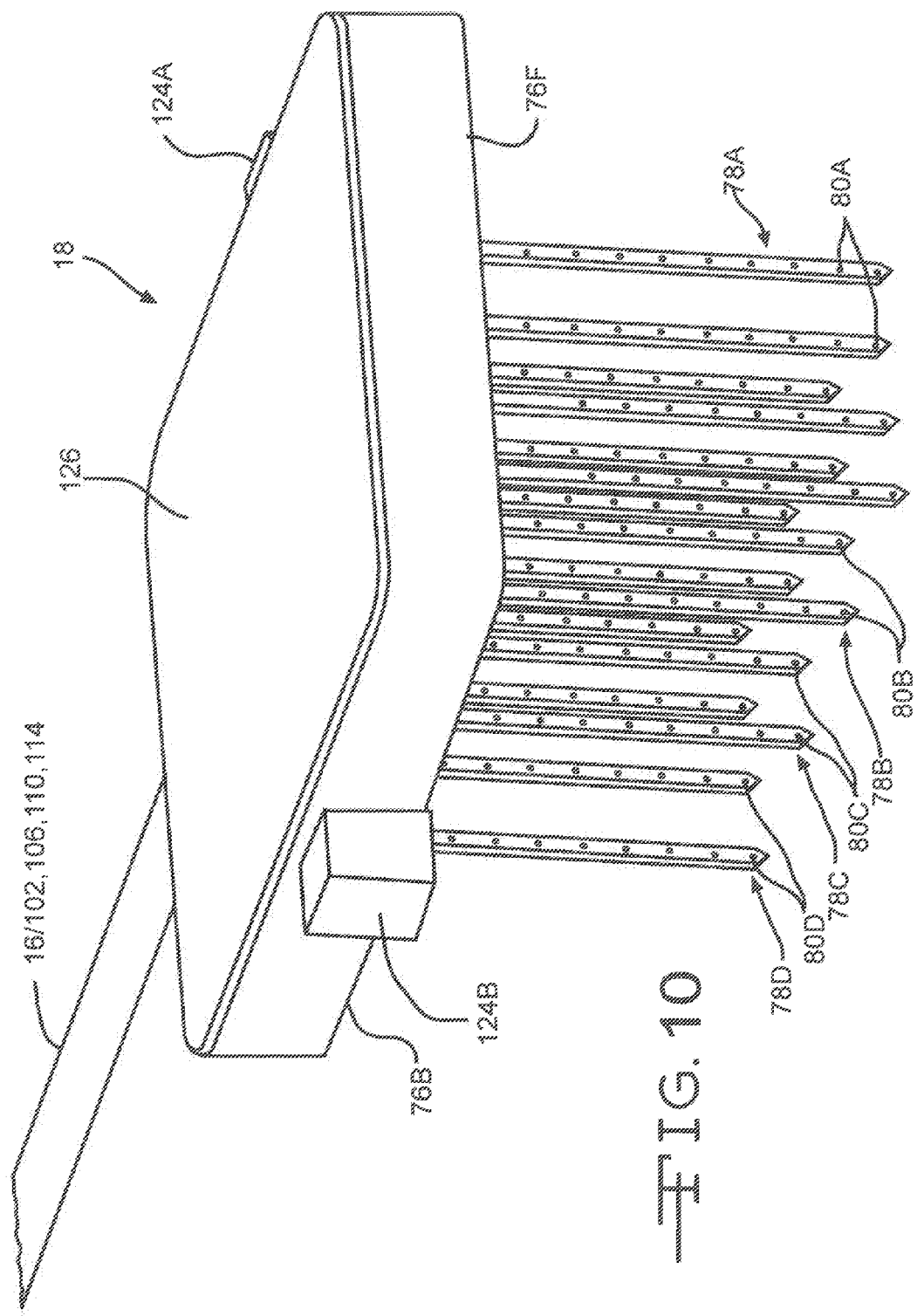
FIG. 10 is a perspective view of a neural probe electrode assembly 18 according to the present invention.

Referring to FIG. 11, locating slots (not shown) are provided in the webs 58, 60 of the cradle 56. Referring to FIG. 10, spaced apart locating ears 124A and 124B are supported on the left and right sidewalls 76A, 76B of the platform 76. A cover 126 is mounted on the upper cover wall 78E to protect the connection between bond plates 100B, 104B, 108B and 112B and their respective ribbon cables 102, 106, 110 and 114.

Figure 12:
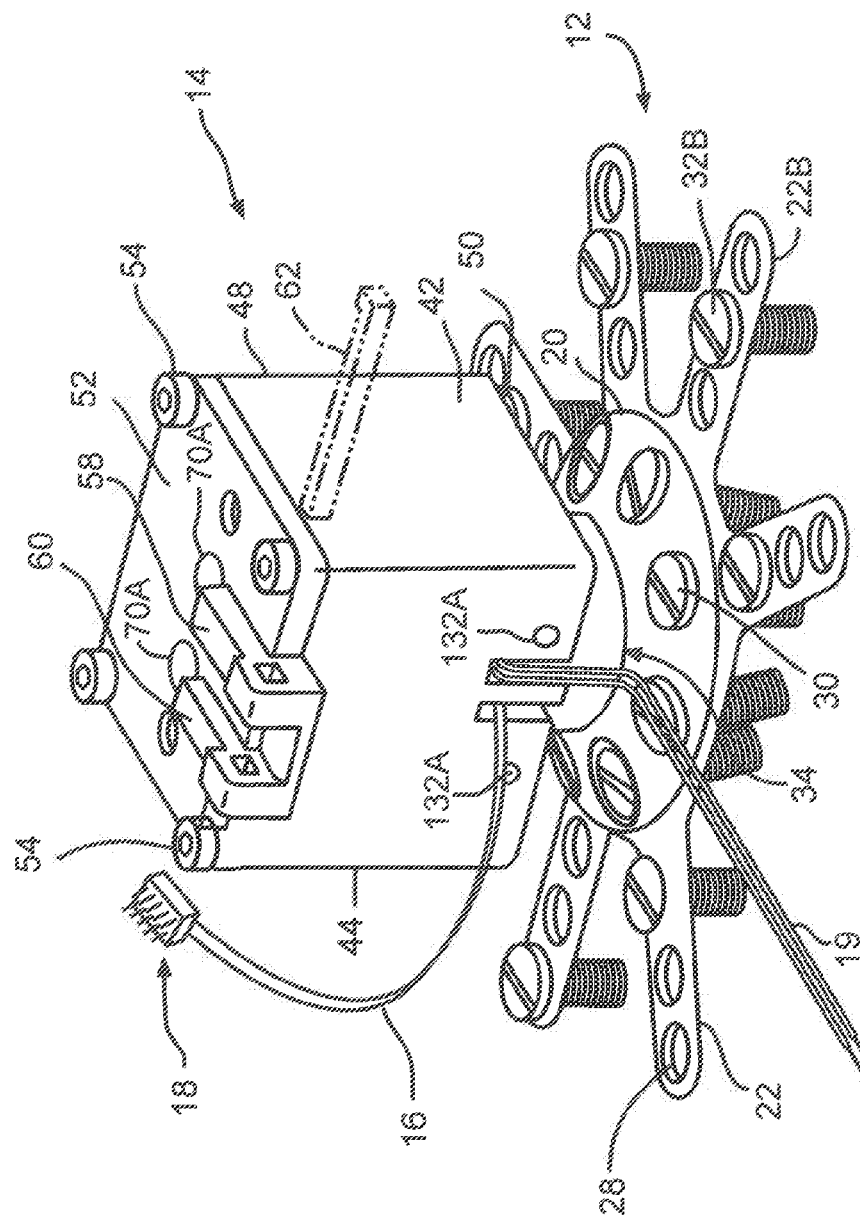
FIG. 12 is a perspective view of the neural probe electrode array system 10 shown in FIG. 11, but with the electrode assembly 18 removed from cradle 56.
Figure 13:
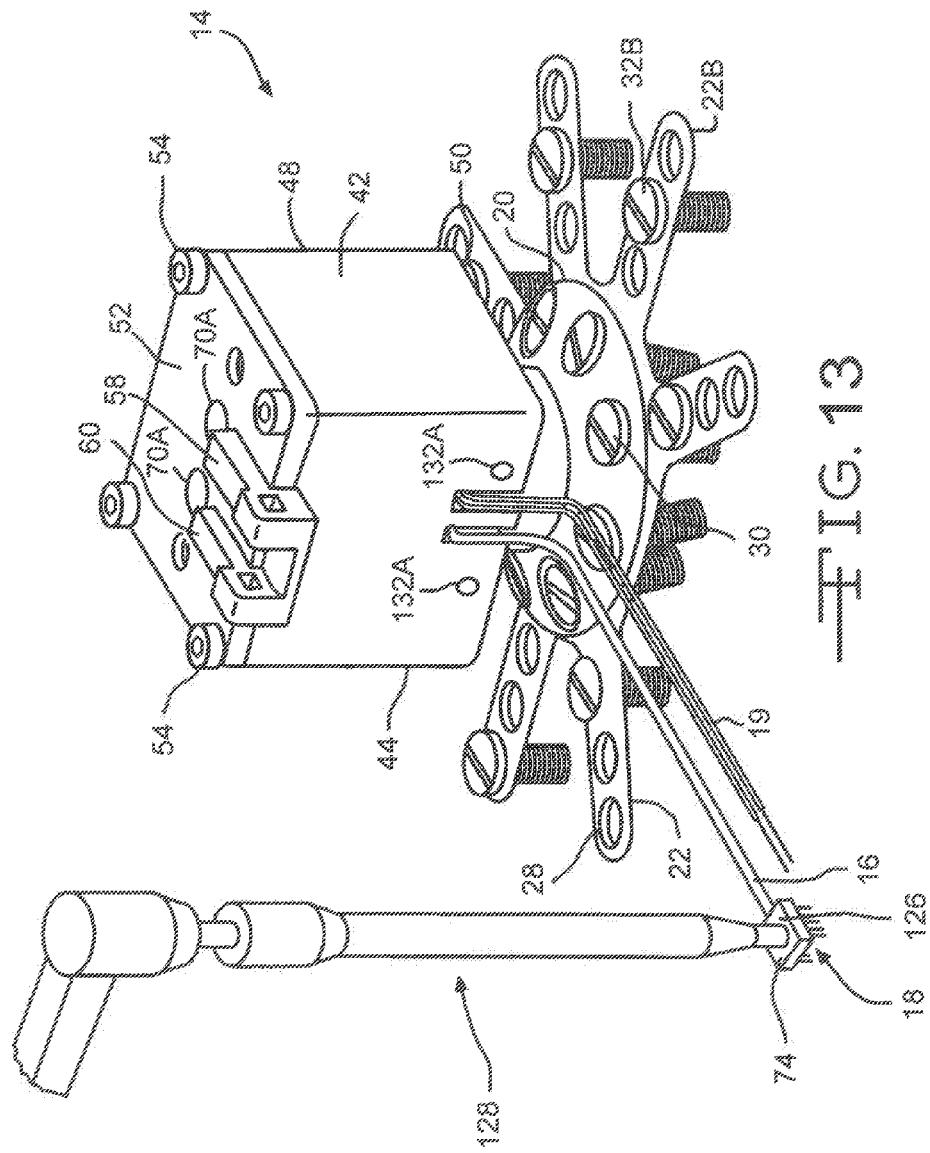
FIG. 13 is a perspective view of the neural probe electrode array system 10 shown in FIG. 12 and with the electrode assembly 18 attached to an actuatable vacuum insertion tool 128.

FIG. 12 illustrates the neural probe electrode array system 10 at the beginning of a surgical procedure. The flexible ribbon cable 16 has its proximal end 16A extending through the face wall 46 to physically and electrically connect to electronic circuits in the housing 14. The distal end of ribbon cable 16 physically and electrically connects to the respective neural probe electrode arrays 100, 104, 108 and 112. Prior to implanting the neural probe electrode assembly 18 into brain tissue, the electrode assembly is nested in the cradle 56 between the spaced apart webs 58, 60. The guard bar 62 blocks the neural probe electrode assembly 18 from inadvertently falling out of the cradle 56 while the secondary cover 64 prevents the array from being damaged during shipping and subsequent assembly of the electronics housing 14 to the skull mounting plate 12.

As shown in FIG. 1A, the mounting plate 12 is secured to the skull 150 adjacent to the access opening 202. That is done using screws 30 and 32 received into the unthreaded openings 24 and 28 of the respective dome-shaped mount body and legs 20, 22. The screws are then threaded into the skull 150. As previously described, the electronics housing 14 is secured to the skull mounting plate 12 with screws 70 received through oversized openings 70A in the cover plate 52 and threaded into openings 38 in the yoke arms 36A, 36B.

With the electronics housing 14 fixedly secured to the mounting plate 12, the neural probe electrode array 18 is ready for implantation into the brain. The secondary cover 64 is removed from the electronics housing 14 by unthreading screws 66 from the housing cover plate 52. The guard bar 62 is manipulated in a direction to remove the L-shaped end 62A from recess 58A in web 58 until the bar is clear of the opening 68 between the webs 58, 60. A pair of tweezers or a similar type tool is used to grab the ribbon cable 16 adjacent to the neural probe electrode assembly 18 and move the cable and electrode assembly out of the cradle 56. The neural probe electrode assembly 18 is turned upside down to access the back face of a platform 76 for the assembly.

FIG. 1A is a schematic view of the neural probe electrode array system 10 mounted to a skull 150 adjacent to a craniotomy opening 202 during a surgical procedure.

An actuatable vacuum insertion tool 128 is maneuvered to grab onto the cove 126 of the platform 76. The insertion tool 128 is a computer-controlled, microsite machine that provides for accurate and controlled insertion of the neural array 18 into the brain tissue. The motor for the insertion tool 128 is designed for fifty millimeters of movement with step depths as small as 0.5 µm. The insertion speed and acceleration are also adjustable.

Figure 14:
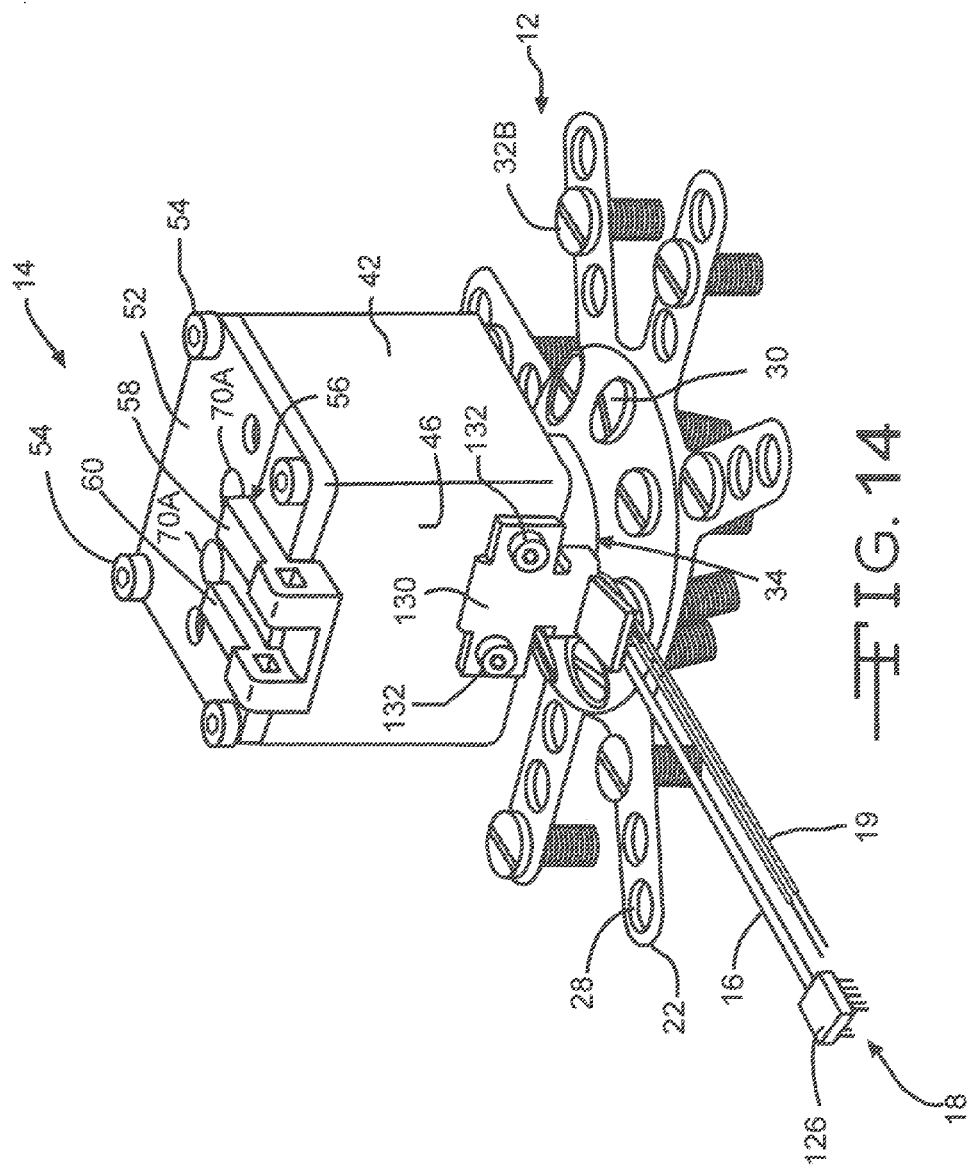
FIG. 14 is a perspective view of the neural probe electrode array system 10 shown in FIG. 13, as the electrode assembly 18 would be positioned in body tissue.

FIG. 14 shows the neural probe electrode assembly 18 as it will appear once insertion into brain tissue is complete. The durotomy and craniotomy are then closed using conventional techniques. Cinching and suturing of skin are performed over the dome-shaped mount body 20 and around the pedestal 34 and underneath gasket 72. A cable guard 130 is secured to the electronic housing 14 using screws 132 extending through openings 132A in face wall 46 and threaded into openings 40 in the arms 36A, 36B of yoke 36.

FIG. 15 illustrates the electronics housing 14, but with the shipping cover plate 52 removed. That is done by unthreading screws 54 from receptacles in the upper edges of the right, left, front and back sidewalls 42, 44, 46 and 48. Four connector assemblies 134A, 134B, 134C and 134D are shown housed inside the housing 14. These connector assemblies serve as interfaces from the respective neural probe electrode assemblies 78A, 78B, 78C and 78D to any one of a number of external devices. Suitable external device include, but are not limited to, a printed circuit board with or without on-board integrated circuits and/or on-chip circuitry for signal conditioning and/or stimulus generation, an Application Specific Integrated Circuit (ASIC), a multiplexer chip, a buffer amplifier, an electronics interface, an implantable rechargeable battery, integrated electronics for either real-time signal processing of the input (recorded) or output (stimulation) signals, integrated electronics for control of a fluidic component, integrated electronics for control of a light source for delivery of light for optogenetic applications, or any other suitable electrical subsystem, or any combination thereof.

Since there is no longer a need to cradle the electrode assembly 18, the shipping cover 52 including its cradle 56 is no longer needed. FIG. 16 shows that the shipping cover 52 is replaced with a top cover 136. The top cover 136 is used throughout the surgical procedure.

Upon completion of the surgical procedure, the skull mounting plate 12 can be removed from the skull or left in place, affixed to the skull. The latter might be desirable if it is determined that a different electronics housing 14 including the flexible cable 16 connected to a different neural probe assembly 18 is desired. For example, that could be for the purpose of using a different neural stimulation protocol or a different configuration for the neural probe arrays comprising the neural probe assembly 18.

FIGS. 17 to 21 illustrate of an exemplary process for manufacturing the platform 76 for the neural probe assembly 18. The process begins with an SOI (silicon-on-insulator) wafer 200, preferably about 500 µm thick. A photo mask (not shown) having interior outlines of the shapes of the respective slots 116, 118, 120 and 122 and their relative orientation to each other is first provided on the upper and lower surfaces of the wafer 200. Wafer 200 consists of a first silicon layer 202, preferably about 100 µm thick, supported on a buried oxide layer 204. The oxide layer 304 is from about 0.5 to 1 µm thick and is sandwiched between the first layer 202 and a second silicon layer 206, which is preferably about 400 µm thick (FIG. 17).

FIG. 18 shows that the first silicon layer 202 has undergone a reactive ion etch (dry etch) to remove portions of the dielectric material, leaving the buried oxide layer 204 exposed between the spaced apart silicon portions 202A and 202B.

In FIG. 19, the patterned silicon layer 202 supported on the oxide layer 204 is turned upside down and temporarily supported on a carrier wafer 208. In FIG. 20, the second silicon layer 206 and the oxide layer 204 are subjected to a further reactive ion etch process. This serves to pattern the second silicon layer into sections 206A, 206B and the oxide layer into corresponding sections 204A, 204B. Relatively thin oxide layers 204A, 204B are supported on the first silicon layers 202A, 202B. As shown, the outer edges of the respective first silicon layer 202, oxide layer 204 and second silicon layer 206 are aligned with each other. This defines previously described the right and left sidewalls 76A, 76B for the platform. Moreover, the inner edges of the first silicon layer and the oxide layer are aligned, but spaced from the inner edge of the second silicon layer. This serves to define where the steps 84A, 84B of the bond pad plate 82 for the exemplary neural probe array 78A reside in the finished neural assembly 18.

FIG. 21 is a cross-sectional view along line 21-21 of FIG. 4 that shows the finished platform section 210 comprising the shaped first silicon layer 202, oxide layer 204 and second silicon layer 206 after having been released from the carrier 208. That is done by dissolving the carrier in a suitable solvent. The resulting open area designated 116 is the slot shown in FIG. 4. The other slots 118, 120 and 122 are manufactured at the same time from the SOI wafer 200. FIG.

21 further illustrates the exemplary thin-film neural probe electrode array 78A in phantom as it would be positioned in slot 116.

Figure 22:
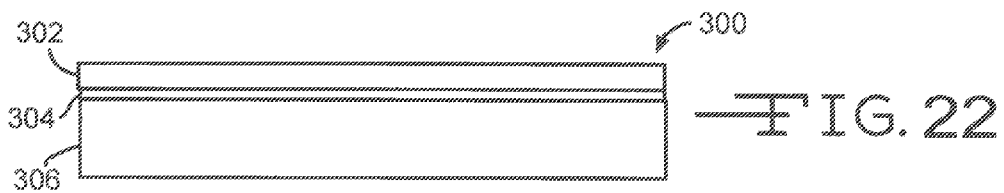
FIGS. 22 to 26 illustrate an exemplary process for manufacturing a cover for the platform 76 shown in FIGS. 4, 7 and 10.

FIGS. 22 to 26 illustrate an exemplary process for manufacturing another embodiment of a cover for the platform 76 shown in FIGS. 4, 7 and 10. The process is similar to that described with respect to FIGS. 17 to 21 for manufacturing the platform 76 and begins with an SOI (silicon-on-insulator) wafer 300, preferably about 500 µm thick. The wafer 300 consists of a first silicon layer 302, preferably about 100 µm thick, supported on an oxide layer 304. The oxide layer 304 is from about 0.5 to 1 µm thick. The oxide layer is sandwiched between the first layer 302 and a second silicon layer 306, preferably about 400 µm thick (FIG. 22).

Figure 23:
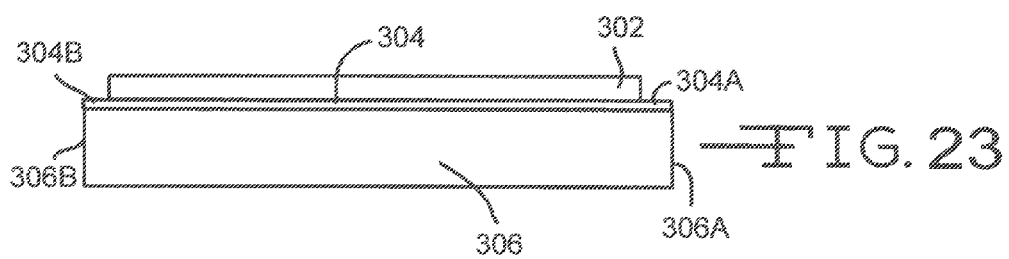

FIG. 23 shows the first silicon layer 302 after having been subjected to a reactive ion etch (dry etch) to remove selected portions thereof. Oxide layer portions 304A and 304B are exposed on opposite sides of a central portion 302. The exposed oxide surfaces 304A, 304B extend to respective edges 306A and 306B of the second silicon layer 306.

Figure 24:
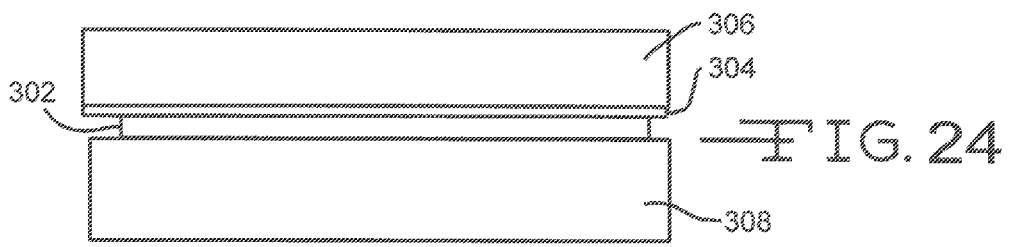

FIG. 24 shows that the wafer consisting of the patterned first silicon layer 302 intermediate the oxide layer 304 after having been turned upside down and supported on a carrier wafer 308.

Figure 25:
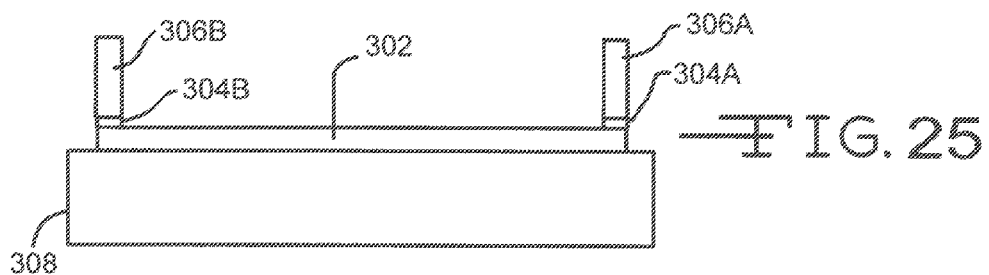
Figure 26:
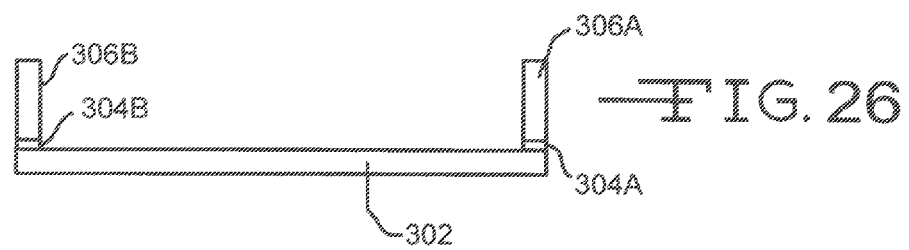

In FIG. 25, the second silicon layer 306 and the oxide layer 304 are subjected to a further reactive ion etch process. This defines upstanding protrusions 306A and 306B supported on oxide layers 304A and 304B. These structures serve as sidewalls for the cover. The carrier wafer 308 is released from the first silicon layer 302 to thereby provide the product cover. If desired, the upstanding protrusions 306A, 306B and their supporting oxide layers 304A, 304B can be eliminated. In that case, a cover similar to that designated as 126 in FIGS. 7 and 10 is the result.

Thus, a three-dimensional neural probe electrode array system is provided. The system consists of an electronics housing that can be detachably mounted to a skull mounting plate affixed to a skull adjacent to a craniotomy. A neural probe assembly connected to the housing consists of a platform supporting a plurality of planar neural probe arrays. When a plurality of two-dimensional neural probe arrays are supported in the platform, the result is a three-dimensional configuration of stimulation and recording electrodes that can be configured for a particular application or surgical procedure. The detachable electronics housing means that, if desired, one neural probe assembly can be changed out for another.

While this invention has been described in conjunction with preferred embodiments thereof, it is evident that many alternatives, modifications, and variations will be apparent to those skilled in the art. Accordingly, the present invention is intended to embrace all such alternatives, modifications and variations that fall within the broad scope of the appended claims.

What is claimed is:

1. A neural probe system, which comprises:
   a) a skull mounting plate, comprising:
      i) a mount body configured to be supported on a skull of a subject; and
      ii) at least two first openings extending through the mount body;
   b) at least two first threaded screws configured for registry in the at least two first openings of the mount body to threadingly mount the skull mounting plate to the skull;
   c) a housing configured to house electronics and to be detachably supported on the skull mounting plate;
   d) an electrical cable extending from a proximal cable portion having a proximal cable end to a distal cable end, wherein the proximal cable end is detachably electrically connected to electronics housed in the housing with the proximal cable portion extending through an opening in the housing;
   e) at least one neural probe electrode assembly comprising a proximal probe end spaced from a distal probe portion having a distal probe end, wherein the proximal probe end is electrically connected to the distal cable end and wherein the distal probe portion has at least one neural probe electrode array configured for electrical stimulation of body tissue or recording of biological characteristics of the body tissue; and
   f) a cradle supported on the housing, wherein the at least one neural probe electrode array is configured to be nested in the cradle prior to placement in a body tissue, and wherein after the housing is supported on the skull mounting plate mounted to the skull by the at least two first threaded screws received in respective ones of the at least two first openings and threaded into the skull, the at least one neural probe electrode array is accessible from outside the housing for placement in a body tissue.

2. The neural probe system of claim 1 wherein the mount body has a dome shape.

3. The neural probe system of claim 1 wherein the skull mounting plate has at least one leg extending outwardly from a perimeter of the mount body.

4. The neural probe system of claim 3 wherein the at least one leg has at least one second opening for receiving a second screw configured for threading into the skull.

5. The neural probe system of claim 4 wherein the at least two first openings of the mount body and the at least one second opening of the at least one leg are unthreaded.

6. The neural probe system of claim 4 wherein the first threaded screws are longer than the second screw.

7. The neural probe system of claim 3 wherein the at least one leg is bendable.

8. The neural probe system of claim 1 wherein a pedestal extending upwardly from the mount body supports a yoke configured for detachable attachment to the housing.

9. The neural probe system of claim 8 wherein the yoke comprises spaced apart upwardly extending arms, and wherein the arms have threaded openings for receiving screws to secure the housing to the skull mounting plate.

10. The neural probe system of claim 1 wherein a gasket resides between the housing and the skull mounting plate.

11. The neural probe system of claim 1 wherein the at least one neural probe electrode array comprises at least one electrode shank extending distally from a bond plate, and at least one electrode supported on the electrode shank.

12. The neural probe system of claim 11 wherein the bond plate supports at least one first bond pad electrically connected to the at least one electrode.

13. The neural probe system of claim 12 wherein the at least one first bond pad supported on the bond plate is physically and electrically connected to a second bond pad at a distal end of the electrical cable.

14. The neural probe system of claim 13 wherein the first bond pad is physically and electrically connected to the second bond pad by a rivet.

15. The neural probe system of claim 14 wherein the at least one neural probe electrode assembly comprises a platform comprising a sidewall providing a thickness extending to spaced apart upper and lower face walls, wherein a slot extending through the thickness of the platform receives the bond plate of the at least one neural probe electrode array with the electrode shank extending distally below the lower face wall.

16. The neural probe system of claim 15 wherein the slot has a first slot portion in open communication with a second slot portion, and wherein the first slot portion has a greater width, but a lesser depth perpendicular to the width than the second slot portion.

17. The neural probe system of claim 16 wherein with the neural probe electrode array received in the slot, a rivet connecting the first bond pad on the bond plate to the second bond pad at the distal end of the electrical cable resides in the depth of the second slot portion.

18. The neural probe system of claim 15, wherein there are at least two slots through the thickness of the platform, each slot supporting a neural probe electrode array, and wherein the two slots are parallel or not parallel to each other.

19. The neural probe system of claim 11 wherein the at least one neural probe electrode array has at least three electrode shanks extending distally from the bond plate.

20. The neural probe system of claim 19 wherein the at least three electrode shanks are of similar or dissimilar lengths.

21. The neural probe system of claim 11 wherein the at least one neural probe electrode array has at least four electrode shanks extending distally from the bond plate, and wherein the electrode shanks are either evenly or unevenly spaced apart from each other.

22. A neural probe system, which comprises:
 a) a skull mounting plate, comprising:
  i) a mount body configured to be supported on a skull of a subject; and
  ii) at least two first openings extending through the mount body; and
 b) at least two first threaded screws configured for registry in the at least two first openings of the mount body to threadingly mount the skull mounting plate to the skull;
 c) a housing comprising a bottom wall supporting a sidewall extending to an upper sidewall edge, wherein the housing is configured to house electronics and to be detachably supported on the skull mounting plate;
 d) an electrical cable extending from a proximal cable portion having a proximal cable end to a distal cable end, wherein the proximal cable end is detachably electrically connected to electronics housed in the housing with the proximal cable portion extending through an opening in the sidewall of the housing; and
 e) at least one neural probe electrode array comprising a proximal probe end spaced from a distal probe portion having a distal probe end, wherein the proximal probe end is electrically connected to the distal cable end and wherein the distal probe portion has at least one neural probe electrode array configured for electrical stimulation of body tissue or recording of biological characteristics of the body tissue;
 f) a detachable cover supported on the upper sidewall edge to provide access to the electronics housed in the housing; and
 g) a cradle supported on the detachable cover, wherein the at least one neural probe electrode array is configured to be nested in the cradle prior to placement in a body tissue, and
 wherein after the housing is supported on the skull mounting plate mounted to the skull by the at least two first threaded screws received in respective ones of the at least two first openings and threaded into the skull, the at least one neural probe electrode array is accessible from outside the housing for placement in a body tissue.

23. The neural probe system of claim 22, wherein the skull mounting plate further comprises:
 a pedestal extending upwardly from the mount body; and
 a yoke supported on the pedestal.

24. The neural probe system of claim 23, wherein the yoke comprises arms with openings for receiving screws to secure the housing to the skull mounting plate.

25. The neural probe system of claim 22, wherein the cradle comprises spaced apart webs that are aligned perpendicular to the sidewall and extend out past the sidewall.

* * * * *